United States Patent
Takase et al.

(10) Patent No.: US 9,283,162 B2
(45) Date of Patent: *Mar. 15, 2016

(54) COMPOSITION FOR OILY FOAMABLE AEROSOL

(75) Inventors: Yoshihiko Takase, Yokkaichi (JP); Kazuhito Uchida, Yokkaichi (JP); Naoteru Honda, Yokkaichi (JP); Tomoharu Kato, Yokkaichi (JP); Nagahiro Yamazaki, Yokkaichi (JP)

(73) Assignee: TAIYO KAGAKU CO., LTD., Yokkaichi-Shi (JP)

( * ) Notice: Subject to any disclaimer, the term of this patent is extended or adjusted under 35 U.S.C. 154(b) by 653 days.

This patent is subject to a terminal disclaimer.

(21) Appl. No.: 10/451,733

(22) PCT Filed: Oct. 24, 2002

(86) PCT No.: PCT/JP02/11040

§ 371 (c)(1),
(2), (4) Date: Jun. 25, 2003

(87) PCT Pub. No.: WO03/035015

PCT Pub. Date: May 1, 2003

(65) Prior Publication Data

US 2004/0197276 A1    Oct. 7, 2004

(30) Foreign Application Priority Data

Oct. 26, 2001  (JP) .................................. 2001-329600
Nov. 30, 2001  (JP) .................................. 2001-365423
Apr. 5, 2002   (JP) .................................. 2002-103976

(51) Int. Cl.
| | |
|---|---|
| *A61K 8/37* | (2006.01) |
| *A61K 8/39* | (2006.01) |
| *A61Q 19/02* | (2006.01) |
| *A61K 8/04* | (2006.01) |

(52) U.S. Cl.
CPC ............... *A61K 8/375* (2013.01); *A61K 8/046* (2013.01); *A61K 8/39* (2013.01); *A61Q 19/02* (2013.01)

(58) Field of Classification Search
CPC ......... A61Q 15/00; A61Q 5/02; A61Q 19/00; A61Q 19/04; A61Q 19/02; A61K 8/046; A61K 8/375; A61K 8/39; A61K 36/28; A61K 47/44

USPC ................ 424/400, 401, 439, 43, 47, 49, 59, 424/78.02, 78.08; 514/844, 846, 937, 943

See application file for complete search history.

(56) References Cited

U.S. PATENT DOCUMENTS

| | | | | |
|---|---|---|---|---|
| 3,770,648 A | * | 11/1973 | Mackles | 516/11 |
| 4,639,367 A | * | 1/1987 | Mackles | 424/45 |
| 5,286,475 A | * | 2/1994 | Louvet et al. | 424/45 |
| 6,278,008 B1 | * | 8/2001 | Endo et al. | 554/227 |
| 6,503,518 B1 | * | 1/2003 | von der Fecht et al. | 424/401 |
| 2001/0024674 A1 | * | 9/2001 | Villagran et al. | 426/550 |
| 2002/0099067 A1 | * | 7/2002 | Posanski | 514/291 |

FOREIGN PATENT DOCUMENTS

| | | | |
|---|---|---|---|
| CA | 2231719 A1 | | 9/1998 |
| JP | 62-266135 A | | 11/1987 |
| JP | 5-70340 A | | 3/1993 |
| JP | 05-078279 A | | 3/1993 |
| JP | 5-213734 A | | 8/1993 |
| JP | 6-100414 A | | 4/1994 |
| JP | 6-329532 A | | 11/1994 |
| JP | 07132222 | * | 5/1995 |
| JP | 8-165218 A | | 6/1996 |
| JP | 9-110636 A | | 4/1997 |
| JP | 2000-080017 | * | 3/2000 |
| JP | 2000-80017 A | | 3/2000 |
| JP | 2000-128734 A | | 5/2000 |
| WO | 99/37282 A2 | | 7/1999 |
| WO | WO-99/37275 A2 | | 7/1999 |
| WO | WO99/37282 | * | 7/1999 |

OTHER PUBLICATIONS

Partial computer trnaslation of JP07132222.*
Macklesumar et al. "Preparation and Surfactant Properties of Diglycerol Esters of Fatty acids", JACOS, vol. 66, No. 1, Jan. 1989.*

* cited by examiner

*Primary Examiner* — Isis Ghali
(74) *Attorney, Agent, or Firm* — Birch, Stewart, Kolasch & Birch, LLP

(57) ABSTRACT

The present invention provides a composition for an oily foamable aerosol, characterized in that the composition comprises a fat or oil, and a polyglycerol fatty acid ester and/or an organic and fatty acid esters of glycerol; and an aerosol comprising the composition as defined in above and a propellant.

22 Claims, No Drawings

COMPOSITION FOR OILY FOAMABLE AEROSOL

TECHNICAL FIELD

The present invention relates to a composition for oily foamable aerosol which is useful as a cleansing agent or the like for oily cosmetics.

BACKGROUND ART

Conventional compositions for aerosol include those which form stable-type foams, fast-disintegrating-type foams, spray-type foams and the like according to the combinations of a stock solution and a propellant. The stable-type foams are constituted by an O/W type emulsion, comprising two phases of an inner phase comprising an oily phase in which a propellant is dissolved, and an aqueous phase having poor compatibility with the propellant. The composition for the foamable aerosol of an O/W emulsion includes cosmetics for cleansing. However, since the cosmetics have low detergency, they have been inappropriate for cleaning oily make-ups. In order to remove oily make-ups, an oily component is most effective, and it is most preferable to obtain a stable-type foam from stock solutions of an oily component and a propellant. However, since the oily component itself is not foamable, it has been difficult to obtain a stable-type foam.

DISCLOSURE OF INVENTION

An object of the present invention is to provide a composition for an oily foamable aerosol which is excellent in detergency, applicability, and favorable wash-up property and stability of the foam.

As a result of intensive studies in order to solve the above-mentioned problems, the present inventors have found that a composition comprising a fat or oil, and a polyglycerol fatty acid ester and/or an organic and fatty acid esters of glycerol is excellent in detergency, applicability, wash-up property and stability of the foam (excellent form-keeping property or form-sustaining property or the like of the foam formed by spraying an aerosol obtained by combining the composition and a propellant, or blowing air into the composition to mix the composition with air. The present invention has been accomplished thereby.

Specifically, the present invention relates to:

[1] a composition for an oily foamable aerosol, characterized in that the composition comprises a fat or oil, and a polyglycerol fatty acid ester and/or an organic and fatty acid esters of glycerol;

[2] the composition according to the above [1], further comprising a phospholipids;

[3] the composition according to the above [1], wherein a constituting fatty acid of the polyglycerol fatty acid ester has 14 or less carbon atoms;

[4] the composition according to any one of the above [1] to [3], wherein the polyglycerol fatty acid ester is a diglycerol fatty acid ester and/or a triglycerol fatty acid ester;

[5] the composition according to any one of the above [1] to [4], wherein the organic and fatty acid esters of glycerol is a succinic and fatty acid esters of glycerol and/or a citric and fatty acid esters of glycerol;

[6] The composition according to any one of the above [1] to [5], wherein a monoester is contained in the polyglycerol fatty acid ester in an amount of 50% by weight or more; and

[7] an aerosol comprising the composition as defined in any one of the above [1] to [6] and a propellant.

BEST MODE FOR CARRYING OUT THE INVENTION

The composition for an oily foamable aerosol (hereinafter referred to as "composition for aerosol") of the present invention is a composition comprising a fat or oil and a specified surfactant. The composition is very excellent in detergency, applicability, wash-up property and stability of the foam, as compared to those of a similar conventional composition for aerosol.

The composition for aerosol of the present invention comprises as essential components a fat or oil, and a polyglycerol fatty acid ester and/or an organic and fatty acid esters of glycerol. There are roughly the following three embodiments.

Embodiment A

A composition for an oily foamable aerosol, characterized in that the composition comprises at least one member of each of a fat or oil, a polyglycerol fatty acid ester and/or an organic and fatty acid esters of glycerol, and a phospholipids.

Embodiment B

A composition for an oily foamable aerosol, characterized in that the composition comprises at least two members selected from the group consisting of a polyglycerol fatty acid ester, an organic and fatty acid esters of glycerol, and a phospholipid, and a fat or oil.

Embodiment C

A composition for an oily foamable aerosol, characterized in that the composition comprises a polyglycerol fatty acid ester of which constituting fatty acid is composed of 14 or less carbon atoms, and a fat or oil.

1. Composition for Aerosol of Embodiment A

The fat or oil is not particularly limited, as long as the fat or oil is in a liquid state during foaming. The fat or oil may be a natural product or a chemically synthesized product. The fat or oil includes oily components such as hydrocarbons, fatty acids, higher alcohols, silicones and esters, besides general liquid fats and oils. Each of the fat or oil can be used alone or in admixture of at least two kinds.

The term "(being) in a liquid state during foaming" as referred to herein means that the fat or oil shows a liquid state at a temperature at which the composition for aerosol is generally used as an aerosol, for instance, 15° C.

The liquid fats and oils include, for instance, avocado oil, camellia oil, turtle oil, macadamia nut oil, corn oil, mink oil, olive oil, rapeseed dil, egg yolk oil, sesame oil, persic oil, wheat germ oil, sasanqua oil, castor oil, linseed oil, safflower oil, cottonseed oil, nettle tree oil, soybean oil, peanut oil, tea oil, kaya oil, rice bran oil, Chinese wood oil, wood oil, jojoba oil, germ oil and the like, and glycerol trioctanoate, glycerol triisopalmitate, and the like. The hydrocarbon includes, for instance, liquid paraffin, squalene, squalane, pristan, and the like. The fatty acid includes, for instance, oleic acid, isostearic acid and the like. The higher alcohol includes, for instance, lauryl alcohol, oleyl alcohol, isostearyl alcohol, octyl dodecanol and the like. The silicone includes, for instance, methyl polysiloxane, methyl phenyl polysiloxane, methyl hydrogen polysiloxane, decamethyl polysiloxane, and the like. The ester includes, for instance, isopropyl myristate, isopropyl palmitate, cetyl octanoate, hexyl laurate, oleyl oleate, decyl oleate, octyl dodecyl myristate, hexyl decyl dimethyloctanoate, diethyl phthalate, dibutyl phthalate and the like. In addition, those obtained by subjecting the above-mentioned fats and oils to such treatments as hydrogen-addition (referred to as hydrogenation in some cases) or separation may be included in the fats and oils. The fat or oil is preferably a combination of one or more kinds of the hydrocarbons and the esters, from the viewpoint of improving detergency for the oily make-ups. The fat or oil may contain an unsaturated fatty acid, side-chain fatty acid, a diglyceride, a monoglyceride or the like as the glyceride component as long as the amount of the glyceride component does not inhibit the exhibition of the desired effects of the present invention.

The content of the fat or oil in the composition for aerosol of the present invention is not particularly limited. The content of the fat or oil is preferably from 10 to 99% by weight, more preferably from 30 to 95% by weight, still more preferably from 60 to 95% by weight.

The polyglycerol of the polyglycerol fatty acid ester includes, but not particularly limited thereto, for instance, glycerol polymers such as diglycerol, triglycerol, tetraglycerol, pentaglycerol, hexaglycerol, heptaglycerol, octaglycerol, nonaglycerol and decaglycerol. The polyglycerol is preferably diglycerol and triglycerol, from the viewpoint of improving stability of the foam. In other words, the polyglycerol fatty acid esters are preferably a diglycerol fatty acid ester and a triglycerol fatty acid ester. Also, the fatty acid of the polyglycerol fatty acid ester is not particularly limited. As the fatty acid, a saturated or unsaturated, linear or branched fatty acid having 8 to 22 carbon atoms and a hydroxy-compound thereof are preferred, and a fatty acid having 14 to 18 carbon atoms is more preferred, from the viewpoint of improving stability of the foam.

As the polyglycerol fatty acid ester, there can be preferably used, for instance, diglycerol myristate, diglycerol palmitate, diglycerol stearate, triglycerol myristate, triglycerol palmitate, triglycerol stearate, and the like.

Each of the polyglycerol fatty acid esters can be used alone or in admixture of at least two kinds. Also, the polyglycerol fatty acid ester may be a mixture of the polyglycerol fatty acid esters having a given esterification degree. The degree of esterification is not particularly limited. When expressed as the monoester content of the mixture, the monoester content is preferably 50% by weight or more, more preferably 70% by weight or more from the viewpoint of improving wash-up property and stability of the foam.

The polyglycerol fatty acid ester is obtained by, for instance, carrying out esterification reaction of a polyglycerol with a fatty acid with heating in the presence of an inert gas such as nitrogen gas in accordance with a known method, and further subjecting the resulting product to distillation and purification as desired, without being limited to this process.

The content of the polyglycerol fatty acid ester in the composition for aerosol of the present invention is not particularly limited. The content of the polyglycerol fatty acid ester is preferably from 0.01 to 50 parts by weight, more preferably from 0.05 to 30 parts by weight, still more preferably from 0.1 to 20 parts by weight, especially preferably from 1 to 20 parts by weight, based on 100 parts by weight of the fat or oil, which is the constituent of the present invention.

Incidentally, when the content of the constituents other than the fat or oil in the composition for aerosol of the present invention is calculated on the basis of the content of the fat or oil, if other oily components besides the constituents of the composition are contained in addition to the fat or oil, the amount of the oily components is included in the amount of the fat or oil.

The organic and fatty acid esters of glycerol refers to a compound in which one or two organic acids are bonded to a glycerol fatty acid ester. When the organic acids are bonded in a plural number, those organic acids may be identical to or different from each other.

The organic acid is not particularly limited. Acetic acid, lactic acid, citric acid, succinic acid and diacetylated tartaric acid are preferred, and citric acid and/or succinic acid is more preferred, from the viewpoint of improving stability of the foam. Especially, an organic and fatty acid esters of glycerol in which one or two succinic acids are bonded to glycerol is preferably used. In other words, as the organic and fatty acid esters of glycerol, a succinic and fatty acid esters of glycerol and a citric and fatty acid esters of glycerol are preferable, and the succinic and fatty acid esters of glycerol is more preferable.

The fatty acid of the organic and fatty acid esters of glycerol is not particularly limited. As the fatty acid, a saturated or unsaturated, linear or branched fatty acid having 8 to 22 carbon atoms, or a hydroxy-compound thereof is preferred, and a fatty acid having 12 to 18 carbon atoms is more preferred, from the viewpoint of improving wash-up property and stability of the foam.

As the organic and fatty acid esters of glycerol, for instance, there can be suitably used succinic and lauric acid esters of glycerol, succinic and myristic acid esters of glycerol, succinic and oleic acid esters of glycerol, succinic and palmitic acid esters of glycerol, succinic and stearic acid esters of glycerol, citric and lauric acid esters of glycerol, citric and myristic acid esters of glycerol, citric and oleic acid esters of glycerol, citric and palmitic acid esters of glycerol, citric and stearic acid esters of glycerol, and the like.

Each of the organic and fatty acid esters of glycerol can be used alone or in admixture of at least two kinds.

The organic and fatty acid esters of glycerol is obtained by, for instance, carrying out esterification reaction of a glycerol fatty acid ester with an organic acid with heating in the presence of an inert gas in accordance with a known method, and further subjecting the resulting product to distillation and purification as desired, without being limited to this process.

The content of the organic and fatty acid esters of glycerol in the composition for aerosol of the present invention is not particularly limited. The content of the organic and fatty acid esters of glycerol is preferably from 0.01 to 50 parts by weight, more preferably from 0.05 to 20 parts by weight, still more preferably from 1 to 10 parts by weight, based on 100 parts by weight of the fat or oil, which is the constituent of the present invention.

At least one of the polyglycerol fatty acid ester or the organic and fatty acid esters of glycerol may be contained in the composition for aerosol of this embodiment. When both the compounds are contained, the mixing ratio of the both compounds (polyglycerol fatty acid ester/organic and fatty acid esters of glycerol) is preferably from 9/1 to 1/9, more preferably from 7/3 to 3/7, on a weight basis. Also, the total content of the polyglycerol fatty acid ester and the organic and fatty acid esters of glycerol is preferably from 0.01 to 50 parts by weight, more preferably from 0.1 to 30 parts by weight, still more preferably from 1 to 20 parts by weight, based on 100 parts by weight of the fat or oil, which is the constituent of the present invention.

As the phospholipid usable in the present invention, natural phospholipids such as egg yolk lecithin, soybean lecithin, rapeseed lecithin, cottonseed lecithin corn lecithin, which are extracted from animals or plants, or hydrogenated products thereof, enzymatically degraded products thereof, acetylated products thereof, hydroxylated products thereof, halogenated products thereof and sulfonated products thereof are preferred. The egg yolk lecithin, the soybean lecithin, or hydrogenated products thereof are more preferable from the viewpoint of improving wash-up property and stability of the foam. Each of those phospholipids can be used alone or in admixture of at least two kinds.

The content of the phospholipid in the composition for aerosol of the present invention is not particularly limited. The content of the phospholipid is preferably from 0.01 to 30 parts by weight, more preferably from 0.05 to 20 parts by weight, still preferably from 1 to 10 parts by weight, based on 100 parts by weight of the fat or oil, which is the constituent of the present invention.

In the composition for aerosol of the present invention, other components can be properly formulated in addition to the above-mentioned components, within the range in which the object of the present invention would be achieved. The other components include, for instance, a known surfactant, a powder of titanium oxide, talc, bentonite, cation and mica, preservatives, coloring agents, antioxidants, perfumes, chemicals and solid oil components other than the above-mentioned fat or oil, semi-solid oily component, alcohols, moisturizing agents, and the like.

As the composition for aerosol of this embodiment, it is especially preferable that the content of the fat or oil is from 60 to 95% by weight, the content of the polyglycerol fatty acid ester and/or the organic and fatty acid esters of glycerol is from 1 to 20% by weight, the content of the phospholipid is from 1 to 10% by weight, and the content of the other components is from 0 to 10% by weight.

2. Composition for Aerosol of Embodiment B

The polyglycerol fatty acid ester, the organic and fatty acid esters of glycerol, the phospholipids, the fat or oil, and optionally formulated other components, which are constituents of the composition for aerosol of this embodiment, and their preferred embodiments and contents are the same as mentioned above.

The composition for aerosol of this embodiment may contain at least two kinds of any one of a polyglycerol fatty acid ester, an organic and fatty acid esters of glycerol and a phospholipid.

For instance, when the polyglycerol fatty acid ester and the organic and fatty acid esters of glycerol are contained, it is preferable that their mixing ratio (polyglycerol fatty acid ester/organic and fatty acid esters of glycerol) is the same as that of the above-mentioned Embodiment A. When the polyglycerol fatty acid ester or the organic and fatty acid esters of glycerol and the phospholipids are contained, their mixing ratio (polyglycerol fatty acid ester or organic and fatty acid esters of glycerol/phospholipids), is preferably from 1/1 to 3/1, more preferably from 1/1 to 2/1, on a weight basis. Also, the total content of any of the two kinds of these components is preferably from 0.02 to 50 parts by weight, more preferably from 0.1 to 30 parts by weight, still more preferably from 1 to 20 parts by weight, based on 100 parts by weight of the fat or oil, which is the constituent of the present invention.

As the composition for aerosol of this embodiment, it is especially preferable that the content of the fat or oil is from 60 to 95% by weight, the content of at least two kinds selected from the group consisting of the polyglycerol fatty acid esters, the organic and fatty acid esters of glycerol and the phospholipids is from 1 to 30% by weight, and the content of the other components is from 0 to 10% by weight.

3. Composition for Aerosol of Embodiment C

The fat or oil, which is the constituent of the composition for aerosol of this embodiment, and its preferred embodiment and content are the same as described above. On the other hand, as the polyglycerol fatty acid ester, those of which constituting fatty acid has 14 or less carbon atoms are used, and its content is 0.1 to 50 parts by weight, more preferably from 1 to 30 parts by weight based on 100 parts by weight of the fat or oil, which is the constituent of the present invention.

The polyglycerol fatty acid ester of which constituting fatty acid has 14 or less carbon atoms refers more specifically to an ester of a saturated or unsaturated, linear or branched fatty acid having 14 or less carbon atoms and a polyglycerol; an ester of a hydroxy-compound of the fatty acid and a polyglycerol; and the like. There can be cited an ester of a fatty acid having preferably 8 to 14 carbon atoms, more preferably 12 or 14, or its hydroxy-compound and a polyglycerol, from the viewpoint of improving detergency and wash-up property of the oily make-up, and stability of the foam. In addition, it is preferable that the polyglycerol, which is a constituting unit, is a diglycerol or a triglycerol. As to the esterification degree of the polyglycerol fatty acid ester, those within the preferred ranges are preferable. The polyglycerol fatty acid ester used in this embodiment includes, for instance, various polyglycerol fatty acid esters exemplified above, of which constituting fatty acid has 14 or less carbon atoms.

As other components, for instance, those exemplified above are used within the range so that the exhibition of the desired effects of the present invention would not be hindered.

As the composition for aerosol of this embodiment, it is especially preferable that the content of the fat or oil is from 60 to 95% by weight, the content of the polyglycerol fatty acid esters of which constituting fatty acid has 14 or less carbon atoms is from 1 to 30% by weight, and the content of the other components is from 0 to 15% by weight.

The composition for aerosol of the present invention as described above can be prepared in accordance with a known method. For instance, the composition can be prepared by appropriately mixing various components mentioned above, heating the components to dissolve them at, for instance, 40° to 80° C. with stirring, and cooling the resulting solution to an ambient temperature.

The application for the composition for aerosol of the present invention includes, but not particularly limited to, for instance, such applications as a detergent for oil stains, a cleansing agent for oily cosmetics, a suntan oil, a baby oil, a hair oil and foamy massage oil and the like, and the application as a cleansing agent is preferable.

The composition for aerosol of the present invention is preferably used as aerosol described below in which the composition is combined with a propellant. On the other hand, since the composition can be foamed by blowing air into the composition to mix the composition with air without formulating a propellant, which is a so-called non-gas type, the composition can be used by packing into a container in which mixing by air-blowing during spraying can be carried out.

The aerosol of the present invention comprises the composition for aerosol of the present invention and an arbitrary propellant, which can be prepared by a known process. For instance, the aerosol can be prepared by introducing the composition for aerosol of the present invention into a given container, and filling the container with a propellant. As the container, for instance, there can be preferably used an aerosol can and the like. Also, as the propellant, there can be preferably used, for instance, chlorofluorocarbons such as trichlorofluoromethane, dichlorodifluoromethane, dichlorofluoromethane, trichlorotrifluoromethane and dichlorotetrafluoromethane; and liquefied gases such as propane, isobutane, isopentane, normal butane and mixtures thereof, which are liquefied petroleum gases (which may be hereinafter referred to as "LPG"). In addition to the above-mentioned propellant, dimethyl ether, carbon dioxide gas, and nitrogen gas may be used as a propellant. Each of the propellants may be used alone or in admixture of at least two kinds. The content of the propellant in the aerosol of the present invention is preferably from 2 to 90% by weight, more preferably from 3 to 90% by weight, still more preferably from 5 to 70% by weight, from the viewpoint of obtaining an excellent foam formation. The content of the composition for aerosol is preferably from 10 to 98% by weight, more preferably from 10 to 97% by weight, still more preferably from 30 to 95% by weight.

Next, the present invention will be described in further detail by means of Examples, without intending to limit the present invention thereto.

Example 1-1

Oily Wash-Away Type Cleansing Oil Cosmetics

Each of oily wash-away type cleansing oil cosmetics was produced by the following process on the basis of the composition of the raw materials shown in Table 1.

TABLE 1

| Raw Materials | Inventive Product A (g) | Inventive Product B (g) | Inventive Product C (g) | Inventive Product D (g) |
| --- | --- | --- | --- | --- |
| 1 Liquid Paraffin | 34.8 | 34.8 | 34.8 | 34.8 |
| 2 Olive Oil | 20 | 20 | 20 | 20 |
| 3 Isopropyl Myristate | 20 | 25 | 25 | 25 |
| 4 Dibutylhydroxytoluene | 0.2 | 0.2 | 0.2 | 0.2 |
| 5 Diglycerol Monopalmitate | 5 | 5 | 5 | — |
| 6 Soybean Lecithin | 5 | 5 | — | 5 |
| 7 Palmitic and Succinic Acid Esters of Glycerol | 5 | — | 5 | 5 |

Ingredients 1 to 7 were heated and dissolved at 80° C., and the resulting solution was cooled to ambient temperature, to give a composition for aerosol of the above-mentioned cosmetics. Thereafter, the composition was packed into an aerosol can, a valve was set thereto, and 10 g of a liquefied petroleum gas was packed therein as a propellant to 90 g of the composition, to give an aerosol of the above-mentioned cosmetics. The resulting cosmetics were referred to as the inventive products A to D, respectively.

Comparative Example 1-1

Oily Wash-Away Type Cleansing Oil Cosmetics

Each of oily wash-away type cleansing oil cosmetics was produced in the same manner as in Example 1-1 on the basis of the composition of the raw materials shown in Table 2.

TABLE 2

| Raw Materials | Comparative Product E (g) | Comparative Product F (g) | Comparative Product G (g) | Comparative Product H (g) |
| --- | --- | --- | --- | --- |
| 1 Liquid Paraffin | 44.8 | 39.8 | 39.8 | 39.8 |
| 2 Olive Oil | 20 | 20 | 20 | 20 |
| 3 Isopropyl Myristate | 25 | 25 | 25 | 25 |
| 4 Dibutylhydroxytoluene | 0.2 | 0.2 | 0.2 | 0.2 |
| 5 Diglycerol Monopalmitate | — | 5 | — | — |
| 6 Soybean Lecithin | — | — | — | 5 |
| 7 Palmitic and Succinic Acid Esters of Glycerol | — | — | 5 | — |

Specifically, aerosols of the above-mentioned cosmetics as comparative products to the inventive products A to D were prepared in the same manner as in the inventive products A to D. The same type oily component-formulated composition as the inventive product but not containing any of polyglycerol fatty acid ester, phospholipid, and organic and fatty acid esters of glycerol is referred to as a comparative product E; the same type oily component-formulated composition containing only polyglycerol fatty acid ester is referred to as a comparative product F; the same type oily component-formulated composition containing only organic and fatty acid esters of glycerol is referred to as a comparative product G; and the same type oily component-formulated composition containing only phospholipid is referred to as a comparative product H.

Test Example 1-1

The inventive products A to D were compared with the comparative products E to H.

As a result, the inventive products A to D formed fine and stable foams. By contrast, the comparative product E did not form foams, and the comparative examples F to H formed rough foams which disappeared immediately.

The results clearly show the followings: The compositions of the present invention had excellent foam stability after spraying, whereas the composition for aerosol not containing polyglycerol fatty acid ester, phospholipid, and organic and fatty acid esters of glycerol (comparative product E) did not form foams. In addition, the compositions containing only one kind of polyglycerol fatty acid ester, phospholipid, and organic and fatty acid esters of glycerol (comparative products F, G, H) formed rough foams and had poor foam stability.

Test Example 1-2

Detergency for the inventive products A to D of Example 1-1 was compared to that of conventional O/W emulsion type foamable aerosol cleansing cosmetics having the raw material composition shown in Table 3.

Ten female panelists were asked to apply an oily foundation. The results of the test for the degree of removal of the foundation are shown in Table 4. Each of the numerical figures in Table 4 shows the number of female panelists which were judged that the foundation was "completely removed," "slightly removed," or "not removed" by the use of each of the cosmetics. Here, "slightly removed" includes a case where the degree of removal of the foundation is insufficient.

TABLE 3

| Raw Materials | Weight (g) |
| --- | --- |
| 1 Polyoxyethylene Lauryl Ether | 10 |
| 2 Liquid Paraffin | 40 |
| 3 Purified Water | Proper Amount |

TABLE 3-continued

| Raw Materials | Weight (g) |
| --- | --- |
| 4 Liquefied Petroleum Gas | 10 |
| 5 Diethyl Ether | 5 |
| Total | 100 |

The O/W emulsion type foamable aerosol cleansing cosmetics were produced by the following process on the basis of the composition of the raw materials shown in Table 3.

Ingredients 1 to 3 were dissolved with stirring. Thereafter, the resulting solution was packed into an aerosol can, a valve was set, and Ingredients 4 and 5 were packed therein, to give an O/W emulsion type aerosol of the above-mentioned cosmetics.

TABLE 4

| | | Completely Removed | Slightly Removed | Not Removed |
| --- | --- | --- | --- | --- |
| Example 1-1 | Inventive Product A | 9 | 1 | 0 |
| | Inventive Product B | 9 | 1 | 0 |
| | Inventive Product C | 9 | 1 | 0 |
| | Inventive Product D | 9 | 1 | 0 |
| O/W Emulsion type Aerosol | | 0 | 2 | 8 |

Table 4 clearly shows the followings: The inventive products A to D had very high detergency as compared to the conventional O/W emulsion type foamable aerosol cleansing cosmetics. Also, the inventive products had the advantages of not dripping when taking onto a palm, easily applying to face, etc. as compared that of conventional pump-type cleansing cosmetics, so that their applicability was excellent. Further, the inventive products had substantially no greasy texture upon wash up, thereby showing excellent wash-up property.

Example 1-2

Suntan Oil

| Raw Materials | Weight (g) |
| --- | --- |
| 1 Octamethyl Cyclotetrasiloxane | 15.0 |
| 2 Decamethyl Cyclopentanesiloxane | 15.0 |
| 3 C11-C15 Alkyl Benzoate | 5.0 |
| 4 Octyl Paradimethylaminobenzoate | 7.0 |
| 5 Oxybenzone | 0.5 |
| 6 Olive Oil | 11.0 |
| 7 Diglycerol Dimyristate | 5.0 |
| 8 Hydrogenated Soybean Lecithin | 5.0 |
| 9 Stearyl Glycyrrhetinate | 0.2 |
| 10 Cetyl Isooctanoate | 21.3 |
| 11 Liquefied Petroleum Gas | 10.0 |
| 12 Diethyl Ether | 5.0 |

Ingredients 1 to 10 were dissolved at 80° C. with stirring, and cooled to ambient temperature, to give a composition for aerosol of a suntan oil. Thereafter, the composition was packed into an aerosol can, a valve was set, and Ingredients 11 and 12 were packed therein, to give an aerosol for the suntan oil. The resulting suntan oil was excellent in foam stability and applicability.

Example 1-3

Wipe-Off Type Cleansing Cosmetics

| Raw Materials | Weight (g) |
| --- | --- |
| 1 Isopropyl Myristate | 42.0 |
| 2 Oleyl Alcohol | 40.0 |
| 3 2-Hydroxy-4-methoxybenzophenone | 3.0 |
| 4 White Vaseline | 2.0 |
| 5 Diglycerol Monomyristate | 7.0 |
| 6 Egg Yolk Lecithin | 6.0 |

Ingredients 1 to 6 were dissolved at 80° C. with stirring, and cooled to ambient temperature, to give a composition for aerosol of the above-mentioned cosmetics. Thereafter, air was blown into and mixed with the resulting cosmetics to foam a foam. As a result, its foam stability was excellent. Also, the cosmetics were excellent in applicability.

Example 1-4

Wash-Away Type Cleansing Cosmetics

| Raw Materials | Weight (g) |
| --- | --- |
| 1 Castor Oil | 19.88 |
| 2 Oleyl Oleate | 15.0 |
| 3 Diethyl Phthalate | 15.0 |
| 4 Tocopherol Acetate | 0.01 |
| 5 Perfume | 0.1 |
| 6 Triglycerol Monopalmitate | 9.0 |
| 7 Enzyme-Degradable Soybean Lecithin | 5.0 |
| 8 Trichlorocarbanilide | 1.0 |
| 9 Stearyl Glycyrrhetinate | 0.01 |
| 10 LPG | 35.0 |

Ingredients 1 to 9 were dissolved at 80° C. with stirring, and cooled to ambient temperature, to give a composition for aerosol of the above-mentioned cosmetics. Thereafter, the composition was packed into an aerosol can, a valve was set, and Ingredient 10 was packed therein, to give an aerosol for the above-mentioned cosmetics. The resulting cosmetics were excellent in foam stability and applicability.

Example 1-5

Wash-Away Type Cleansing Cosmetics

| Raw Materials | Weight (g) |
| --- | --- |
| 1 Castor Oil | 19.88 |
| 2 Oleyl Oleate | 15.0 |
| 3 Diethyl Phthalate | 10.0 |
| 4 Tocopherol Acetate | 0.01 |
| 5 Perfume | 0.1 |
| 6 Triglycerol Monopalmitate | 9.0 |
| 7 Enzyme-Degradable Soybean Lecithin | 5.0 |
| 8 Palmitic and Succinic Acid Esters of Glycerol | 5.0 |
| 9 Trichlorocarbanilide | 1.0 |
| 10 Stearyl Glycyrrhetinate | 0.01 |
| 11 LPG | 35.0 |

Ingredients 1 to 10 were dissolved at 80° C. with stirring, and cooled to ambient temperature, to give a composition for aerosol of the above-mentioned cosmetics. Thereafter, the composition was packed into an aerosol can, a valve was set, and Ingredient 11 was packed therein, to give an aerosol for the above-mentioned cosmetics. The resulting cosmetics were excellent in foam stability and applicability.

Example 1-6

Baby Oil

| Raw Materials | Weight (g) |
| --- | --- |
| 1 Squalane | 34.44 |
| 2 Oleyl Alcohol | 20.0 |
| 3 Polymethylsiloxane | 5.0 |
| 4 Stearyl Glycyrrhetinate | 0.01 |
| 5 Beeswax | 0.5 |
| 6 Tocopherol Acetate | 0.05 |
| 7 Monooleic and Disuccinic Acid Esters of Glycerol | 5.0 |
| 8 Soybean Lecithin | 5.0 |
| 9 Trichlorotrifluoromethane | 20.0 |
| 10 Dimethyl Ether | 10.0 |

Ingredients 1 to 8 were dissolved at 80° C. with stirring, and cooled to ambient temperature, to give a composition for aerosol of a baby oil. Thereafter, the composition was packed into an aerosol can, a valve was set, and Ingredients 9 and 10 were packed therein, to give an aerosol for the baby oil. The resulting baby oil was excellent in foam stability and applicability.

Example 1-7

Hair Oil

| Raw Materials | Weight (g) |
| --- | --- |
| 1 Camellia Oil | 30.0 |
| 2 Hexyl Laurate | 22.0 |
| 3 Tocopherol Acetate | 0.01 |
| 4 Perfume | 0.5 |
| 5 Monopalmitic and Disuccinic Acid Esters of Glycerol | 4.0 |
| 6 Soybean Lecithin | 4.0 |
| 7 Trichlorofluoromethane | 40.0 |
| 8 Nitrogen gas | 0.1 |

Ingredients 1 to 6 were dissolved at 80° C. with stirring, and cooled to ambient temperature, to give a composition for aerosol of a hair oil. Thereafter, the composition was packed into an aerosol can, a valve was set, and Ingredients 7 and 8 were packed therein, to give an aerosol for the hair oil. The resulting hair oil was excellent in foam stability and applicability.

Example 1-8

Hair Oil

| Raw Materials | Weight (g) |
| --- | --- |
| 1 Camellia Oil | 30.0 |
| 2 Hexyl Laurate | 22.0 |
| 3 Tocopherol Acetate | 0.01 |
| 4 Perfume | 0.5 |
| 5 Monopalmitic and Disuccinic Acid Esters of Glycerol | 4.0 |
| 6 Diglycerol Monolaurate | 4.0 |
| 7 Trichlorofluoromethane | 40.0 |
| 8 Nitrogen gas | 0.1 |

Ingredients 1 to 6 were dissolved at 80° C. with stirring, and cooled to ambient temperature, to give a composition for aerosol of a hair oil. Thereafter, the composition was packed into an aerosol can, a valve was set, and Ingredients 7 and 8 were packed therein, to give an aerosol for the hair oil. The resulting hair oil was excellent in foam stability and applicability.

Example 1-9

Foamy Massage Oil Cosmetics

| Raw Materials | Weight (g) |
| --- | --- |
| 1 Liquid Paraffin | 52.0 |
| 2 Polyoxyethylene Glyceryl Triisostearate | 4.0 |
| 3 Squalane | 10.0 |
| 4 Perfume | 0.8 |
| 5 Macadamia Nut Oil | 5.0 |
| 6 Isostearyl Glycyrrhetinate | 0.1 |
| 7 Monopalmitic and Disuccinic Acid Esters of Glycerol | 4.0 |
| 8 Diglycerol Monolaurate | 4.0 |
| 9 Trichlorofluoromethane | 20.0 |
| 10 Nitrogen gas | 0.1 |

Ingredients 1 to 8 were dissolved at 80° C. with stirring, and cooled to ambient temperature, to give a composition for aerosol of the above-mentioned cosmetics. Thereafter, the composition was packed into an aerosol can, a valve was set, and Ingredients 9 and 10 were packed therein, to give an aerosol for the above-mentioned cosmetics. The resulting cosmetics were excellent in foam stability and applicability.

Example 2-1

Oily Wash-Away Type Cleansing Oil Cosmetics

Each of oily wash-away type cleansing oil cosmetics was produced by the following process on the basis of the composition of the raw materials shown in Table 5.

TABLE 5

| Raw Materials | Inventive Products (g) | | | | | | |
| --- | --- | --- | --- | --- | --- | --- | --- |
| | A | B | C | D | E | F | G |
| 1 Liquid Paraffin | 34.8 | 34.8 | 34.8 | 34.8 | 34.8 | 34.8 | 34.8 |
| 2 Olive Oil | 25 | 20 | 20 | 20 | 20 | 20 | 20 |
| 3 Isopropyl Myristate | 25 | 25 | 25 | 25 | 20 | 20 | 20 |
| 4 Dibutylhydroxy-toluene | 0.2 | 0.2 | 0.2 | 0.2 | 0.2 | 0.2 | 0.2 |
| 5 Diglycerol Monomyristate | 5 | — | 5 | 5 | — | 5 | 5 |
| 6 Diglycerol Monolaurate | — | 10 | — | — | — | — | — |
| 7 Diglycerol Monocaprate | — | — | 5 | — | 5 | — | — |

TABLE 5-continued

| Raw Materials | Inventive Products (g) | | | | | | |
|---|---|---|---|---|---|---|---|
| | A | B | C | D | E | F | G |
| 8 Triglycerol Monolaurate | — | — | — | 5 | 10 | — | 5 |
| 9 Triglycerol Monomyristate | — | — | — | — | — | 10 | 5 |

Ingredients 1 to 9 were mixed, and heated and dissolved at 80° C., and the resulting solution was cooled to ambient temperature, to give a composition for aerosol of the above-mentioned cosmetics. Thereafter, the composition was packed into an aerosol can, a valve was set thereto, and 10 g of a liquefied petroleum gas was packed therein as a propellant to 90 g of the composition, to give an aerosol of the above-mentioned cosmetics. The resulting cosmetics were referred to as the inventive products A to G, respectively.

Comparative Example 2-1

Oily Wash-Away Type Cleansing Oil Cosmetics

Each of oily wash-away type cleansing oil cosmetics was produced by the following process on the basis of the composition of the raw materials shown in Table 6.

TABLE 6

| Raw Materials | Comparative Products (g) | | | | |
|---|---|---|---|---|---|
| | H | I | J | K | L |
| 1 Liquid Paraffin | 44.8 | 39.8 | 39.8 | 39.8 | 39.8 |
| 2 Olive Oil | 20 | 20 | 20 | 20 | 20 |
| 3 Isopropyl Myristate | 25 | 25 | 25 | 25 | 25 |
| 4 Dibutylhydroxytoluene | 0.2 | 0.2 | 0.2 | 0.2 | 0.2 |
| 5 Polyoxyethylene(6) Oleyl Ether | — | 10 | — | — | — |
| 6 Triglycerol Monopalmitate | — | — | 10 | — | — |
| 7 Diglycerol Monostearate | — | — | — | 10 | — |
| 8 Diglycerol Monopalmitate | — | — | — | — | 10 |

*The number inside the parenthesis ( ) in Raw Material 5 shows the number of moles of ethylene oxide added, hereinafter the same.

Compositions for aerosols and aerosols were obtained in accordance with the method described in Example 2-1 using Raw Materials 1 to 8. Here, the product not containing a surfactant is referred to as a comparative product H; a product containing polyoxyethylene(6) oleyl ether, Raw Material 5, is referred to as a comparative product I; a product containing triglycerol monopalmitate, Raw Material 6, is referred, to as a comparative product J; a product containing diglycerol monostearate, Raw Material 7, is referred to as a comparative product K; and a product containing diglycerol monopalmitate, Raw Material 8, is referred to as a comparative product L.

Test Example 2-1

The inventive products A to G were compared with the comparative products H to L. The evaluation methods and the evaluation criteria are as follows.

State of Foam Formation

The state of foam formation was observed by naked eyes. The evaluations were: those which are excellent were noted with ○, and those which are poor were noted with x. The case where fine foams were formed when each of the aerosol was sprayed on the acrylic plate (length: 10 cm, width 10 cm) was judged "excellent," and other cases were judged "poor."

Foam Stability

The maintenance of the formed foams was evaluated. The evaluations were: those which are excellent were noted with ○, and those which are poor were noted with x. The case where the foams substantially did not disappear for at least one minute after spraying each aerosol was judged "excellent," and other cases were judged "poor."

Wash-Up Property

The wash-up property during water rinsing was evaluated. The evaluations were: those which are excellent were noted with ○, and those which are poor were noted with x. One female panelist was asked to apply an oily foundation, and the foundation was cleansed with each of the cosmetics, and the cosmetics were further washed away with water. The case where the foundation can be completely washed away without giving at least a greasy wash-away state was judged "excellent," and other cases were judged "poor."

The results are shown in Table 7.

TABLE 7

| | | State of Foam Formation | Foam Stability | Wash-Up Property |
|---|---|---|---|---|
| Example 2-1 | Inventive Product A | ○ | ○ | ○ |
| | Inventive Product B | ○ | ○ | ○ |
| | Inventive Product C | ○ | ○ | ○ |
| | Inventive Product D | ○ | ○ | ○ |
| | Inventive Product E | ○ | ○ | ○ |
| | Inventive Product F | ○ | ○ | ○ |
| | Inventive Product G | ○ | ○ | ○ |
| Comparative Example 2-1 | Comparative Product H | X | X | X |
| | Comparative Product I | X | X | X |
| | Comparative Product J | X | X | X |
| | Comparative Product K | X | X | X |
| | Comparative Product L | X | X | X |

It is clear from Table 7 that the inventive products A to G formed stable fine foams, and gave excellent wash-up, whereas the comparative products H to L formed rough foams and gave much greasy texture during wash-up.

Test Example 2-2

Detergency for the inventive products A to G of Example 2-1 was compared to that of the above-mentioned conventional O/W emulsion type foamable aerosol cleansing cosmetics.

Ten female panelists were asked to apply an oily foundation. The results for the test for the degree of removal of the foundation are shown in Table 8.

TABLE 8

|  |  | Completely Removed | Slightly Removed | Not Removed |
|---|---|---|---|---|
| Example 2-1 | Inventive Product A | 9 | 1 | 0 |
|  | Inventive Product B | 9 | 1 | 0 |
|  | Inventive Product C | 9 | 1 | 0 |
|  | Inventive Product D | 9 | 1 | 0 |
|  | Inventive Product E | 9 | 1 | 0 |
|  | Inventive Product F | 9 | 1 | 0 |
|  | Inventive Product G | 9 | 1 | 0 |
| O/W Emulsion type Aerosol |  | 0 | 2 | 8 |

Table 8 clearly shows the followings: The inventive products A to G had very high detergency as compared to the conventional O/W emulsion type foamable aerosol cleansing cosmetics. Also, the inventive products had the advantages of not dripping when taking onto a palm, and easily applying to face, etc. as compared those of conventional pump-type cleansing cosmetics, so that their applicability was excellent. Further, the inventive products had substantially no greasy texture upon wash up, thereby showing excellent wash-up property.

Example 2-2

Suntan Oil

| Raw Materials | Weight (g) |
|---|---|
| 1 Octamethyl Cyclotetrasiloxane | 15.0 |
| 2 Decamethyl Cyclopentanesiloxane | 15.0 |
| 3 C11-C15 Alkyl Benzoate | 5.0 |
| 4 Octyl Paradimethylaminobenzoate | 7.0 |
| 5 Oxybenzone | 0.5 |
| 6 Olive Oil | 11.0 |
| 7 Diglycerol Monomyristate | 10.0 |
| 8 Stearyl Glycyrrhetinate | 0.2 |
| 9 Cetyl Isooctanoate | 21.3 |
| 10 Liquefied Petroleum Gas | 10.0 |
| 11 Diethyl Ether | 5.0 |

Raw Materials 1 to 9 were mixed and dissolved at 80° C. with stirring, and cooled to ambient temperature, to give a composition for aerosol of a suntan oil. Thereafter, the composition was packed into an aerosol can, a valve was set, and Raw Materials 10 and 11 were packed therein, to give an aerosol for the suntan oil. The resulting suntan oil was excellent in foam stability and applicability.

Example 2-3

Wipe-Off Type Cleansing Cosmetics

| Raw Materials | Weight (g) |
|---|---|
| 1 Isopropyl Myristate | 42.0 |
| 2 Oleyl Alcohol | 40.0 |
| 3 2-Hydroxy-4-methoxybenzophenone | 3.0 |
| 4 White Vaseline | 2.0 |
| 5 Diglycerol Monolaurate | 3.0 |
| 6 Liquefied Petroleum Gas | 10.0 |

Raw Materials 1 to 5 were mixed and dissolved at 80° C. with stirring, and cooled to ambient temperature, to give a composition for aerosol of the above-mentioned cosmetics. Thereafter, the composition was packed into an aerosol can, a valve was set, and Raw Material 6 was packed therein, to give an aerosol for the above-mentioned cosmetics. The resulting cosmetics were excellent in foam stability and applicability.

Example 2-4

Wash-Away Type Cleansing Cosmetics

| Raw Materials | Weight (g) |
|---|---|
| 1 Castor Oil | 19.88 |
| 2 Oleyl Oleate | 15.0 |
| 3 Diethyl Phthalate | 10.0 |
| 4 Tocopherol Acetate | 0.01 |
| 5 Perfume | 0.1 |
| 6 Triglycerol Monomyristate | 5.0 |
| 7 Diglycerol Monolaurate | 9.0 |
| 8 Diglycerol Monocaprylate | 5.0 |
| 9 Trichlorocarbanilide | 1.0 |
| 10 Stearyl Glycyrrhetinate | 0.01 |
| 11 Liquefied Petroleum Gas | 35.0 |

Raw Materials 1 to 10 were mixed and dissolved at 80° C. with stirring, and cooled to ambient temperature, to give a composition for aerosol of the above-mentioned cosmetics. Thereafter, the composition was packed into an aerosol can, a valve was set, and Raw Material 11 was packed therein, to give an aerosol for the above-mentioned cosmetics. The resulting cosmetics were excellent in foam stability and applicability.

Example 2-5

Baby Oil

| Raw Materials | Weight (g) |
|---|---|
| 1 Squalane | 34.44 |
| 2 Oleyl Alcohol | 20.0 |
| 3 Polymethylsiloxane | 5.0 |
| 4 Stearyl Glycyrrhetinate | 0.01 |
| 5 Beeswax | 0.5 |
| 6 Tocopherol Acetate | 0.05 |
| 7 Polyoxyethylene(1) Lauryl Ether Phosphate | 5.0 |
| 8 Diglycerol Monolaurate | 5.0 |
| 9 Liquefied Petroleum Gas | 20.0 |
| 10 Dimethyl Ether | 10.0 |

Raw Materials 1 to 8 were mixed and dissolved at 80° C. with stirring, and cooled to ambient temperature, to give a composition for aerosol of a baby oil. Thereafter, the composition was packed into an aerosol can, a valve was set, and Raw Materials 9 and 10 were packed therein, to give an aerosol for the baby oil. The resulting baby oil was excellent in foam stability and applicability.

Example 2-6

Hair Oil

| Raw Materials | Weight (g) |
|---|---|
| 1 Camellia Oil | 30.0 |
| 2 Hexyl Laurate | 22.0 |
| 3 Tocopherol Acetate | 0.01 |
| 4 Perfume | 0.5 |
| 5 Diglycerol Monocaprylate | 2.0 |
| 6 Diglycerol Monomyristate | 6.0 |
| 7 Liquefied Petroleum Gas | 39.39 |
| 8 Nitrogen gas | 0.1 |

Raw Materials 1 to 6 were mixed and dissolved at 80° C. with stirring, and cooled to ambient temperature, to give a composition for aerosol of a hair oil. Thereafter, the composition was packed into an aerosol can, a valve was set, and Raw Materials 7 and 8 were packed therein, to give an aerosol for the hair oil. The resulting hair oil was excellent in foam stability and applicability.

Example 2-7

Foamy Massage Oil Cosmetics

| Raw Materials | Weight (g) |
|---|---|
| 1 Liquid Paraffin | 52.0 |
| 2 Polyoxyethylene Glyceryl Triisostearate | 4.0 |
| 3 Squalane | 10.0 |
| 4 Perfume | 0.8 |
| 5 Macadamia Nut Oil | 5.0 |
| 6 Isostearyl Glycyrrhetinate | 0.1 |
| 7 Diglycerol Monocaprate | 2.0 |
| 8 Diglycerol Monolaurate | 6.0 |
| 9 Liquefied Petroleum Gas | 20.0 |
| 10 Nitrogen gas | 0.1 |

Raw Materials 1 to 8 were mixed and dissolved at 80° C. with stirring, and cooled to ambient temperature, to give a composition for aerosol of the above-mentioned cosmetics. Thereafter, the composition was packed into an aerosol can, a valve was set, and Raw Materials 9 and 10 were packed therein, to give an aerosol for the above-mentioned cosmetics. The resulting cosmetics were excellent in foam stability and applicability.

INDUSTRIAL APPLICABILITY

The composition for aerosol provided by the present invention is useful as a cleansing agent for oily cosmetics, and the composition is excellent in detergency, applicability, wash-up property and foam stability.

The invention claimed is:
1. A cosmetic comprising:
(1) a composition for aerosol comprising:
(a) an oil composition consisting essentially of oily components selected from a fat or oil in an amount that is 60 to 99% by weight of the composition for aerosol; and
(b) 1 to 30 parts by weight of diglycerol monolaurate, based on 100 parts by weight of the fat or oil, wherein the monoester content is 50% by weight or more, wherein no water is added upon preparation of the aerosol composition as a whole; and
(2) a pressurized aerosol propellant.
2. A cosmetic comprising:
(1) a composition for aerosol comprising:
(a) an oil composition consisting essentially of oily components selected from a fat or oil in an amount of 60 to 99% by weight of the composition for aerosol;
(b) 1 to 20 parts by weight of diglycerol monolaurate, based on 100 parts by weight of the fat or oil, wherein the monoester content is 50% by weight or more; and
(c) a phospholipid,
wherein no water is added upon preparation of the aerosol composition as a whole; and
(2) a pressurized aerosol propellant.
3. The cosmetic of claim 2, which further comprises an organic and fatty acid ester of glycerol.
4. The cosmetic according to claim 1 or 2, wherein the fat or oil comprises at least one member selected from the group consisting of avocado oil, camellia oil, turtle oil, macadamia nut oil, corn oil, mink oil, olive oil, rapeseed oil, egg yolk oil, sesame oil, persic oil, wheat germ oil, sasanqua oil, castor oil, linseed oil, safflower oil, cottonseed oil, nettle tree oil, soybean oil, peanut oil, tea oil, kaya oil, rice bran oil, Chinese wood oil, wood oil, jojoba oil, germ oil, glycerol trioctanoate and glycerol triisopalmitate.
5. The cosmetic according to claim 1 or 2, wherein the fat or oil includes at least one hydrocarbon selected from the group consisting of liquid paraffin, squalene, squalane and pristan.
6. The cosmetic according to claim 1 or 2, wherein the fat or oil includes at least one fatty acid selected from the group consisting of oleic acid and isostearic acid.
7. The cosmetic according to claim 1 or 2, wherein the fat or oil includes at least one higher alcohol selected from the group consisting of lauryl alcohol, oleyl alcohol, isostearyl alcohol and octyl dodecanol.
8. The cosmetic according to claim 1 or 2, wherein the fat or oil includes at least one silicone selected from the group consisting of methyl polysiloxane, methyl phenyl polysiloxane, methyl hydrogen polysiloxane and decamethyl polysiloxane.
9. The cosmetic according to claim 1 or 2, wherein the fat or oil includes at least one ester selected from the group consisting of isopropyl myristate, isopropyl palmitate, cetyl octanoate, hexyl laurate, oleyl oleate, decyl oleate, octyl dodecyl myristate, hexyl decyl dimethyloctanoate, diethyl phthalate and dibutyl phthalate.
10. The cosmetic according to claim 1 or 2, wherein the propellant is at least one selected from the group consisting of trichlorofluoromethane, dichlorodifluoromethane, dichlorofluoromethane, trichlorotrifluoromethane, dichlorotetrafluoromethane, propane, isobutane, isopentane, normal butane, dimethyl ether, carbon dioxide gas and nitrogen.
11. The cosmetic according to claim 1 or 2, wherein the cosmetic is a cleansing oil.
12. A cosmetic consisting essentially of:
(1) a composition for aerosol comprising:
(a) an oil composition comprising a fat or oil that is in a liquid state at 15° C., wherein the amount of the fat or oil is 60 to 99% by weight of the composition for aerosol;

(b) 1 to 30 parts by weight of diglycerol monolaurate, based on 100 parts by weight of the fat or oil, wherein the monoester content is 50% by weight or more; and (c) optionally one or more components selected from the group consisting of phospholipid, surfactant, powder of titanium oxide, powder of talc, powder of bentonite, powder of cation, powder of mica, preservative, coloring agent, antioxidant, perfume, solid oil components, alcohol, and moisturizing agent, wherein no water is added upon preparation of the aerosol composition as a whole; and (2) a pressurized aerosol propellant.

13. The cosmetic of claim 12, which is a cleansing agent for oily cosmetics.

14. The cosmetic of claim 12, which is a suntan oil.

15. The cosmetic of claim 12, which is a baby oil.

16. The cosmetic of claim 12, which is a hair oil.

17. The cosmetic of claim 12, which is a foamy massage oil.

18. The cosmetic of claim 12, which is an aerosol composition containing said pressurized propellant packaged in an aerosol can with a valve.

19. The cosmetic of claim 13, which is an aerosol composition containing said pressurized propellant packaged in an aerosol can with a valve.

20. The cosmetic according to claim 3, wherein the organic and fatty acid esters of glycerol is a succinic and fatty acid esters of glycerol and/or a citric and fatty acid esters of glycerol.

21. The cosmetic of claim 1 or 2, wherein the monoester content in the polyglycerol fatty acid ester is 70% by weight or more.

22. The cosmetic of claim 12, wherein the monoester content in the polyglycerol fatty acid ester is 70% by weight or more.

* * * * *